(12) United States Patent
Minor et al.

(10) Patent No.: US 9,420,816 B2
(45) Date of Patent: *Aug. 23, 2016

(54) HIGH PROTEIN LIQUID ENTERAL NUTRITIONAL COMPOSITION

(71) Applicant: N.V. Nutricia, Zoetermeer (NL)

(72) Inventors: Marcel Minor, Wageningen (NL); Koenraad Gerard Christoffel Weel, Ede (NL); Natalie Elizabeth Hotrum, Oneonta, NY (US)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,085

(22) Filed: Jul. 21, 2014

(65) Prior Publication Data

US 2014/0364361 A1    Dec. 11, 2014

Related U.S. Application Data (62) Division of application No. 12/921,694, filed as application No. PCT/NL2009/050120 on Mar. 12, 2009, now Pat. No. 8,815,797.

(30) Foreign Application Priority Data

Mar. 12, 2008  (NL) .................. PCT/NL2008/050141

(51) Int. Cl.
  *A23L 1/29*     (2006.01)
  *A23L 1/305*    (2006.01)

(52) U.S. Cl.
  CPC ............... *A23L 1/296* (2013.01); *A23L 1/293* (2013.01); *A23L 1/305* (2013.01); *A23L 1/3055* (2013.01); *A23L 1/3056* (2013.01); *A23V 2002/00* (2013.01)

(58) Field of Classification Search
  CPC ....................................................... A23L 1/296
  See application file for complete search history.

(56) References Cited

U.S. PATENT DOCUMENTS

| | | | |
|---|---|---|---|
| 3,764,711 A | 10/1973 | Melnychyn et al. | |
| 3,843,828 A | 10/1974 | Arndt | |
| 4,112,123 A | 9/1978 | Roberts | |
| 4,497,836 A | 2/1985 | Marquardt et al. | |
| 5,256,437 A | 10/1993 | Degen et al. | |
| 5,514,655 A | 5/1996 | DeWille et al. | |
| 5,641,531 A | 6/1997 | Liebrecht et al. | |
| 5,683,984 A | 11/1997 | Jost | |
| 5,780,039 A | 7/1998 | Greenberg et al. | |
| 5,948,452 A | 9/1999 | Monte | |
| 6,383,551 B1 | 5/2002 | Foegeding et al. | |
| 6,774,111 B1 | 8/2004 | Wolf et al. | |
| 7,247,320 B2 | 7/2007 | Jost | |
| 7,858,028 B2 | 12/2010 | Pijls | |
| 7,868,042 B2 | 1/2011 | Romanczyk et al. | |
| 8,409,651 B2 | 4/2013 | Sliwinski et al. | |
| 2003/0022863 A1 | 1/2003 | Stahl et al. | |
| 2003/0077357 A1 | 4/2003 | Rizvi et al. | |
| 2003/0099761 A1 | 5/2003 | Jost | |
| 2004/0057867 A1 | 3/2004 | Pijls | |
| 2004/0258823 A1 | 12/2004 | Dufresne et al. | |
| 2006/0051296 A1 | 3/2006 | Holahan | |
| 2007/0104760 A1 | 5/2007 | Yokawa et al. | |
| 2007/0128341 A1 | 6/2007 | Bakkene et al. | |
| 2007/0154614 A1 | 7/2007 | Sherwood et al. | |
| 2007/0202153 A1 | 8/2007 | Molenaar | |
| 2009/0162494 A1 | 6/2009 | Lai | |
| 2010/0216740 A1 | 8/2010 | Stahl et al. | |
| 2010/0286020 A1 | 11/2010 | Calame et al. | |
| 2014/0011742 A1 | 1/2014 | Sedman et al. | |

FOREIGN PATENT DOCUMENTS

| | | |
|---|---|---|
| AU | 2172288 B | 3/1989 |
| EP | 0 322 96 | 7/1981 |
| EP | 0 833 27 | 7/1983 |
| EP | 0 323 529 A1 | 7/1989 |
| EP | 0 438 783 A2 | 7/1991 |
| EP | 0 486 425 A2 | 5/1992 |
| EP | 0 686 396 B1 | 1/1995 |
| EP | 0 747 395 A1 | 12/1996 |
| EP | 1 151 754 B1 | 11/2001 |
| EP | 1 314 361 A1 | 5/2003 |
| EP | 1 351 587 A1 | 10/2003 |
| EP | 1 563 741 A1 | 8/2005 |
| EP | 1 654 934 A1 | 5/2006 |
| EP | 1 787 528 A1 | 5/2007 |
| EP | 1 839 492 B1 | 10/2007 |
| EP | 2 230 941 A1 | 9/2010 |
| EP | 2 612 561 A1 | 7/2013 |

(Continued)

OTHER PUBLICATIONS

"Enhanced weight gain system, advanced recovery formula drink mix" Elite Image Nutrition, [Online] 2002, XP002515496—Retrieved from the Internet: http://www.beverlyintl.com/weight-gainer-massmaker.html> [retrieved on Feb. 17, 2009], 4 pages.

"Evaluation and Definition of Potentially Hazardous Foods—Chapter 3. Factors that influence Microbial Growth", Safe Practices for Food Processes (Auszug Internet FDA), 2014.

"Milk Protein Concentrate Ingredients," [Online] 2003, Retrieved from the Internet: http://www.innovatewithdiary.com/NR/rdonlyres/37F8B376-A74F-4DE6-BC8F-3B238A823A95/0/G5IngredientSpecMPC.pdf> retrieved on Feb. 20, 2009, pp. 1-2, XP002516236.

"Muscle Milk, Nature's Ultimate Growth Formula" IFAST400 Monster Maker, [Online] Jul. 23, 2003, Retrieved from the Internet: http://www.1fast400.com/p433_Mass_Maker_Beverly_International.html> , retrieved on Feb. 20, 2009, p. 1-3, XP002516238.

Aerosol—Wikipedia—http://en.wikipedia.org/wiki/Aerosol, dated Jan. 6, 2014.

(Continued)

*Primary Examiner* — Amber D Steele (74) *Attorney, Agent, or Firm* — Foley & Lardner LLP; Sunit Talapatra (57) ABSTRACT

The present invention relates in general to a shelf-stable liquid enteral composition for providing nutrition, either as a supplement, or as a complete nutrition, with a high protein content of a non-hydrolyzed globular protein, in particular a whey protein.

21 Claims, 5 Drawing Sheets

(56) References Cited

FOREIGN PATENT DOCUMENTS

| | | |
|---|---|---|
| GB | 1 277 772 | 6/1972 |
| JP | 11-018723 | 1/1999 |
| WO | WO-93/03754 | 3/1993 |
| WO | WO-93/08697 | 5/1993 |
| WO | WO-95/17830 | 7/1995 |
| WO | WO-97/11614 | 4/1997 |
| WO | WO-98/07328 | 2/1998 |
| WO | WO-99/56563 | 11/1999 |
| WO | WO-01/60378 A2 | 8/2001 |
| WO | WO-02/15720 A2 | 2/2002 |
| WO | WO-02/052166 | 7/2002 |
| WO | WO-02/098242 A1 | 12/2002 |
| WO | WO-03/043446 | 5/2003 |
| WO | WO-03/055334 A1 | 7/2003 |
| WO | WO-03/084340 A1 | 10/2003 |
| WO | WO-2004/054371 | 7/2004 |
| WO | WO 2004/060342 | 7/2004 |
| WO | WO-2005/039597 A2 | 5/2005 |
| WO | WO-2005/082170 A1 | 9/2005 |
| WO | WO-2006/034857 | 4/2006 |
| WO | WO-2006/042222 | 4/2006 |
| WO | WO-2006/058083 A2 | 6/2006 |
| WO | WO-2006/058538 A1 | 6/2006 |
| WO | WO-2006/120155 A1 | 11/2006 |
| WO | WO-2007/027213 A1 | 3/2007 |
| WO | WO-2007/047592 | 4/2007 |
| WO | WO-2007/082267 | 7/2007 |
| WO | WO-2007/108827 A1 | 9/2007 |
| WO | WO-2007/110411 A2 | 10/2007 |
| WO | WO-2007/110421 A2 | 10/2007 |
| WO | WO-2007/136263 | 11/2007 |
| WO | WO-2008/041219 A1 | 4/2008 |
| WO | WO-2008/136420 A1 | 11/2008 |
| WO | WO-2009/011573 A1 | 1/2009 |
| WO | WO-2009/072869 A1 | 6/2009 |
| WO | WO-2009/072884 A1 | 6/2009 |
| WO | WO-2009/072885 A1 | 6/2009 |
| WO | WO-2009/072886 A1 | 6/2009 |
| WO | WO-2009/113845 A1 | 9/2009 |
| WO | WO-2009/113858 A1 | 9/2009 |
| WO | WO-2009/150183 | 12/2009 |

OTHER PUBLICATIONS

Affirmation of Alistair James Carr, dated Dec. 24, 2013, 10 pgs.
Affirmation of Stephen Murray Taylor, dated Dec. 24. 2013, 10 pgs.
Alizadehfard, M. et al. "Viscosity of Whey Protein Solutions", Iranian J Polymer Science and Technology, 1995, vol. 4, No. 2, pp. 126-133.
Anonymous, "Nepro Specialized Complete Balanced Nutrition," date unknown, found at http://rpdcon40.ross.com/mn/.../C668F1C5D1267DF105256CDE0048A266?OpenDocumen, 8 pages.
Anonymous, "Nestle VHC (Very High Calorie) 2.25 Carnation Instant Breakfast, Lactose Free," date unknown, retrived from internet, www.vitalitymedical.com/nestle-vhc-very-high-calorie-2-25-carnation-instant-breakfast-lactose-free, 5 pages.
Anonymous, "Pro-Cal Shot," date unknown, retrieved from internet, www.vitafloweb.com, 2 pages.
Arla Foods—Wikipedia—http://en.wikipedia.org/wiki/Arla_Foods, dated Dec. 17, 2013.
Bipro—"Whey protein isolate" —Jan. 6, 2014, (https://www.google.de/search?q=Bipro%22whey protein isolate%22 filetype%3A).
Burrington, "High-Powered Protein Drinks," Food Product Design [Online], Oct. 1, 2001: http://www.foodproductdesign.com/articles/2001/10/high-powered-protein-drinks.aspx.
Chantapornchai et al. "Influence of a NaCl on optical properties, large-strain rheology and water holding capacity of heat-induced whey protein isolate gels", Food Hydrocolloids, 2002, vol. 16, pp. 467-476.
Chen, J. et al. "Viscoelastic Properties of Heat-Set Whey Protein Emulsion Gels", Journal of Texture Studies, 1998, vol. 29, pp. 285-304.
Demetriades, K. et al. "Influence of pH and Heating on Physicochemical properties of Whey Protein-Stabilized Emulsions Containing a Nonionic Surfactant", J. Agric. Food Chem., 1998, vol. 46, pp. 3936-3942.
Demetriades, K. et al. "Physical Properties of Whey Protein Stabilized Emulsions as Related to pH and NaCl", Journal of Food Science, 1997, vol. 62, No. 2, pp. 342-347.
Dewan et al., "Viscosity and Voluminosity of Bovine Milk Casein Micelles", Department of Biochemistry, Department of Food Science and Industries, University of Minnesota, Jun. 30, 1972, pp. 699-705, 7 pages.
Dunford, "Sports Nutrition: A Practice Manual for Professionals," 4th Ed., 2006, pp. 130-131 (best available copy—view at http://www.google.com/search?tbm=bks&hl=e& q=marie+dunford+increasing+casein+protein+and+health+ benefits&btnG=).
Eilers, "Die Viskosität von Emulsionen hochviskoser Stoffe als Funktion der Konzentration," Kolloid Z, 1941, 97(3)313-321.
Eilers, "Die Viskositäts-Konzentrationsabhängigkeit kolloider Systeme in organischen Lösungsmitteln," Kolloid Z, 1943, 102(2):154-169.
Euston, S. et al. "Aggregation kinetics of heated whey protein-stabilized emulsions", Food Hydrocolloids, 2000, vol. 14, pp. 155-161.
Ferreira et al., "Instrumental Method for Characterizing Protein Foams," J Food Sci, 1995, 60(1):90-93.
Foegeding, E. et al. "Fcators that determine the fracture properties and microstructure of globular protein gels", Food Hydrocolloids, 1995, vol. 9, No. 4, pp. 237-249.
Hunt, J. et al. "Heat Stability of Oil-in-Water Emulsions Containing Milk Proteins: Effect of Ionic Strength and pH", Journal of Food Science, 195, vol. 60, No. 5, pp. 1120-1131.
Karlsson et al., "Relationship Between Physical Properties of Casein Micelles and Rheology of Skim Milk Concentrate,"J. Dairy Sci., vol. 88, Nov. 1, 2005, pp. 3784-3797, 14 pages.
Laere, "Degradation of Structurally different non-digestible oligosaccharides by intestinal bacteria: glycosylhydrolases of Bi. adolescentis." PhD-thesis (2000), Wageningen Agricultural University, Wageningen, The Netherlands.
Marshall, K. "Therapeutic Applications of Whey Protein", Alternative Medicine Review, 2004, vol. 9, No. 2, pp. 136-156.
McDougall et al., "The Whey Proteins of the Milk of Red Deer (Cervus elaphus L.), A Homologue of Bovine β-Lactoglobulin," Biochem. J., vol. 153, Mar. 1, 1976, pp. 647-655.
Melo et al., Effect of Ultra-High-Temperature Steam Injection on Model Systems of a α-Lactalbumin and β-Lactoglobulin, J Dairy Sci, 1978, 61(6):710-713.
Milch—Wikipedia—http://de.wikipedia.org/wiki/Milch, dated Jan. 6, 2014.
Milk protein concentrate—Wikipedia—http://en.wikipedia.org/wiki/Milk_protein_concentrate, dated Jan. 6, 2014.
Monkos, "Determination of Some Hydrodynamic Parameters of Ovine Serum Albumin Solutions Using Viscometric Measurements," J Biol Phys, 2005, 31(2):219-232.
Monkos, "On the Hydrodynamics of Dimeric Bovine Beta-Lactoglobulin Solutions from Viscometry Approach," Polish J. of Environ. Stud., vol. 15, No. 4A, Sep. 20, 2006, pp. 88-90.
Notice of Opposition (Arla Foods Amba)in EP Appln No. 09718670.4 dated Jan. 10, 2014.
Notice of Opposition (Fonterra Co-Operative Group Limited) in EP Appln No. 09718670.4 dated Jan. 9, 2014.
Notion of Opposition (Friesland Brands B.V.) in EP Appln No. 09718670.4 dated Jan. 10, 2014.
Notice of Opposition (Nestec SA) in EP Appln No. 09718670.4 dated Jan. 10, 2014.
Pap, et al. "Waste minimization and utilization in the food industry: Processing of arctic berries, and extraction of valuable compounds from juice-processing by-products", Jun. 10, 2004, University of Oulu, Finland, Oulu University Press: Oulu pp. 159-168.
Parker et al., "Effects of Added Sodium Caseinate on the Formation of Particles in Heated Milk," J Agric Food Chem, 2005, 53(21):8265-8272.

(56) References Cited

OTHER PUBLICATIONS

Pasteurisierung—Wikipedia—http://de.wikipedia.org/wiki/Pasteurisierung, dated Dec. 11, 2013.

Sodinin et al., "Milk and milk-based dairy ingredients,"Manufacturing Yogurt and Fermented Milks 2006, pp. 167-178, Blackwell Publishing [XP002497557] on line url:http://books.google.nl/books?id=IroZmON2tHsC&pg=PA167&lpg=PA167&dq=sodini,milk-based dairy ingredients&source=web&ots=SpCQK9-5Zy&sig=ydp-1P7trkP40Eosf7Sbt6LzDPQ&h1=en&sa=X&oi=book_result&resnum=1&ct=result>.

Souci, et al. —"Food composition amd Nurtrition Tables", MedPharm Scientific Publishers, 2008, 171-174.

Spagnuolo PA et al., Kappa-carrageenan interactions in systems containing casein micelles and polysaccharide stabilizers. Food Hydrocolloids, Elsevier, vol. 19, No. 3, May 1, 2005.

Velez-Ruiz et al, "Rheological Properties of Concentrated Milk as a Function of Concentration, Temperature and Storage Time," J Food Eng, 1998, 35:177-190.

Walstra et al. "Dairy Science and Technology," 2nd Ed, The Free Library, Retrieved Jan. 21, 2011 from http://www.thefreelibrary.com/Dairy+science+and+technology,+2d+ed.-a0139423256.

Whey protein—Wikipedia, Oct. 16, 2013, 3 pgs.

Wijesinha-Bettoni, R. et al. "Heat Treatment of Bovine alpha-Lactalbumin Results in Partially Folded, Disulfide Bond Shuffled States with Enhanced Surface Activity", Biochemistry, 2007, vol. 46, pp. 9774-9784.

Ye, A. et al. "Characterization of cold-set gels produced from heated emulsions stabilized by the whey protein", International Dairy Journal, 2009, vol. 19, pp. 721-727.

Zayas, "Functionality of Proteins in Food", Springer-Verlag Berlin Heidelberg GmbH, 1997, Chapter 1.

HIGH PROTEIN LIQUID ENTERAL NUTRITIONAL COMPOSITION

CROSS-REFERENCE TO RELATED APPLICATION(S)

This application is a Divisional of U.S. patent application Ser. No. 12/921,694, filed as National Phase of International Patent Application No. PCT/NL2009/050120, filed Mar. 12, 2009 which claims priority to International Patent Application No. PCT/NL2008/050141, filed Mar. 12, 2008. The contents of these applications are herein incorporated by reference in their entirety.

FIELD OF THE INVENTION

This invention is concerned with a method for the heat-treatment of a non-hydrolysed globular protein, the non-hydrolysed heat-treated globular protein per se, a shelf-stable liquid enteral nutritional composition with a high content of non-hydrolysed globular protein as a major protein source, processes for the preparation thereof and use of said liquid enteral nutritional composition for the treatment of persons in need thereof.

BACKGROUND OF THE INVENTION

Clinical Problem

Some patients need nutrition, either as a supplement, or as a complete nutrition, in the smallest volume of liquid.

These patients can be cachectic patients or persons suffering from end-stage AIDS, cancer or cancer treatment, severe pulmonary diseases like COPD (chronic obstructive pulmonary disease), tuberculosis and other infection diseases or persons that experienced severe surgery or trauma like burns. Furthermore, persons suffering from disorders in the throat or mouth such as oesophageal cancer or stomatitis and persons having problems with swallowing like dysphagic persons, require special liquid, low-volume nutrition. Also, persons just suffering from reduced appetite or loss of taste, will benefit from low-volume, preferably liquid, food. These patients can also be elderly persons, in particular frail elderly and elderly at risk of becoming frail. In this regard, although an elderly person's energy needs may be reduced, their ability to consume products may also be diminished. For example, they may have difficulty consuming a product due to, e.g., swallowing difficulties, or due the too large amount of product they need to consume to meet the daily intake of nutrients. Hence, compliance is not optimal, and often, the intake is suboptimal, leading to suboptimal nourishment, and in the end, to malnutrition.

In this respect, it is submitted that in the context of this application, an elderly person is a person of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

The aforementioned groups of patients may be extremely sensitive to food consistency and to the organoleptic properties of the product such as, for instance viscosity, mouth feel, taste, smell and colour. Also, patients such as cachectic patients, typically suffer from extreme weakness which often prevents them from sitting in a vertical position and from their ability to drink the food from a carton or even to suck it from a straw. These patients benefit well from liquid low-volume enteral compositions with a high content of nutrients.

Therefore, the problem underlying the present invention is to provide a shelf-stable liquid enteral composition for providing nutrition, either as a supplement, or as a complete nutrition, with a high content of non-hydrolysed globular protein as major protein source, in particular whey proteins, in the smallest volume of liquid, and which supports nutrition and well-being in the different patient groups mentioned above.

In the context of the current application, enteral means any form of administration that involves any part of the gastrointestinal tract, i.e. by mouth (orally), by gastric feeding tube, duodenal feeding tube, or gastrostomy, and rectally.

Technical Problem

Major technical difficulties exists in producing such a shelf-stable liquid enteral nutritional composition with a high content of non-hydrolysed globular proteins, in particular non-hydrolysed whey proteins.

For example, increasing the amount of proteins leads to precipitation and sedimentation of proteins and other ingredients, such as lipids and carbohydrates, which imparts nutrient intake.

Concentrating liquids also increases the chance of undesired interactions between ingredients which reduces stability, especially during heating and long-term storage.

Furthermore, increasing the protein content in a nutritional liquid composition may increase the overall viscosity of the composition. This can make the liquid nutritional composition difficult to consume or administer, and can also diminish the taste of the nutritional composition. These phenomena often follow non-linear kinetics and the problems quickly increase in magnitude when the concentration of ingredients is increased above 28 weight %. Therefore, many of the commercial shelf-stable liquid products that are currently available have intact protein levels below about 9 g per 100 ml of product.

A known solution to the problem how to increase the protein levels to a higher level without imparting viscosity is replacing part of the total protein by peptides or free amino acids. However, this seriously decreases taste appreciation and therefore voluntary intake of the nutritional composition by the patient group.

On the other hand, many concentrates like condensed milks suffer from an incomplete nutrient profile, too high lactose levels, sticky mouth-feel, high viscosity, extreme sweetness and a high osmotic value, which is not appreciated by the consumer and increases rapidly feelings of fullness and satiety after consumption. This makes that the urge to consume more volume deteriorates rapidly once a small amount of the product has been consumed.

EP 0 486 425 A2 (Sandoz Nutrition, published 20 May 1992) discloses a liquid nutritional composition comprising 3.9 weight % of WPC having an energy density of 1.0 kcal/ml.

EP 0 747 395 (Nestle S. A, published 11 Dec. 1996) discloses a product for treating renal patients having an energy density of 1.6-2.25 kcal/ml and comprising free amino acids and whey proteins, wherein the ratio of essential amino acids to non-essential amino acids is 2-4:1. By using free amino acids, the amino acid composition is improved without increasing the viscosity. However, the taste is not acceptable for cachectic persons or other persons which have difficulties in eating the proper volume of food. The amount of protein is about 3 to 4 g/100 ml of product.

EP 1 314 361 (Nestec S. A., published 28 May 2005, also published as US 2003/099761) discloses a nutritionally complete calorically dense formula comprising maximum 8 g/100 ml intact whey protein using WPI as a source of whey (Example 1). An intermediate composition containing 9.2 weight. % whey protein is acidified to a pH of 3.0, UHT treated at 148° C. for 5 seconds followed by dilution with a base to pH 6.8. This solution is subsequently mixed with the usual ingredients (lipids, carbohydrates, minerals) to provide a nutritional composition.

WO 2007/110411 and WO 2007/110421 (Nestec S. A., published Oct. 4, 2007) disclose heat-treated whey protein micelles, obtained by a process which comprises a pH adjustment and a heat-treatment between 70° C. and 95° C.

EP 1 787 528 (Kraft Foods Holdings Inc, published May 23, 2007) discloses a method of deflavoring whey protein using membrane electrodialysis. The deflavored whey protein materials are said to be suitable for use in dairy and non-dairy beverages, smoothies, health drinks, cheese cheese analogs, dairy and non-dairy yoghurts, meat and meat analog products, cereals, baked products, snacks and the like. The document mentions the use of the deflavored whey protein in liquid food products to provide about 2.5 to about 30 g whey protein per single liquid serving of about 100 to about 300 ml. However, the document does not disclose how to prepare liquid food products with a high concentration of protein that enables achieving stable liquid food products upon sterilization or pasteurization. Without taking appropriate measures, it is not possible to prepare sterilized or pasteurized liquid food products with a whey protein concentration of for example 30 g per 100 ml.

SUMMARY OF THE INVENTION

In one embodiment, the present invention relates in general to a shelf-stable liquid enteral composition for providing nutrition, either as a supplement, or as a complete nutrition, with a high protein content of a non-hydrolysed globular protein, in particular a whey protein.

In one embodiment, the present invention provides a shelf-stable liquid enteral nutritional composition based mainly on non-hydrolysed globular proteins, designed to meet the nutritional needs of persons in need thereof, in particular elderly, persons recovering from certain disease states, and malnourished persons. The composition provides an increased amount of proteins per unit volume while providing a sufficiently low viscosity to allow the composition to be easily consumed orally or be administered by tube. In addition, the taste of the composition is not diminished in comparison with a less concentrated composition based on non-hydrolysed whey proteins.

To this end, in a first embodiment of the present invention, a liquid enteral nutritional composition is provided, in particular a sterilized or pasteurized liquid enteral nutritional composition, comprising i) 9 to 20 g of non-hydrolysed globular protein per 100 ml of the composition having a pH>3 and ≤8; ii) 10 to 20 g of non-hydrolysed globular protein per 100 ml of the composition; iii) 9 to 20 g of non-hydrolysed globular protein per 100 ml of the composition, with the proviso that a UHT-sterilized composition comprising 9.2 weight % whey protein having a pH=3 is excluded. In particular, said globular protein is a whey protein.

In a second embodiment, the present invention concerns a method of providing nutrition to a person in need thereof, in particular elderly, persons recovering from certain disease states, and malnourished persons, comprising the steps of administering to said person the nutritional composition according to the present invention.

In a third embodiment, the present invention concerns a process for the heat-treatment of non-hydrolysed globular proteins, to obtain heat-treated non-hydrolysed globular proteins with unique properties. In particular, said heat-treated non-hydrolysed globular protein is a whey protein.

The unique properties allow not only the manufacture of a nutritional composition comprising 9 to 20 g of heat-treated non-hydrolysed globular per 100 ml of the composition, but the unique heat-treated non-hydrolysed globular protein is suitable for use in any nutritional composition comprising these unique heat-treated globular proteins as a protein source in any concentration. Therefore, in a fourth embodiment, the present invention concerns the unique heat-treated non-hydrolysed globular proteins per se, obtainable by the process according to the invention, and any product, formulation or composition comprising said heat-treated globular proteins, in particular whey proteins.

The invention will now be further elucidated by describing a number of embodiments of the present invention.

DETAILED DESCRIPTION OF THE INVENTION

Globular Proteins

The invention is generally concerned with globular proteins. Globular proteins may be single chains, two chains or more chains which interact in the usual ways or there may be portions of the chains with helical structures, pleated structures, or completely random structures. Globular proteins are relatively spherical in shape as the name implies. They are distributed in both plant and animal tissues. For instance, albumins can be found in blood (serum albumin), milk (lactalbumin), egg white (ovalbumin), lentils (legumelin), kidney beans (phaseolin), and wheat (leucosin). Globulins can be found in blood (serum globulins), muscle (myosin), potato (tuberin), Brazil nuts (excelsin), hemp (edestin), whey (lactoglobulins, immunoglobulins, and lactoferrins), pea and lentils (legumin, vicilin), and soy. Also, many enzymes and other vegetable proteins are globular proteins.

More specifically, the invention is concerned with pea, soy and whey proteins, more in particular with whey proteins.

Whey Proteins

One of the most superior classes of food protein is whey protein. It is known for its excellent amino acid profile, high cystein content, rapid digestion, and interesting bioactive proteins (lactoglobulins, immunoglobulins, and lactoferrins). Nutritionally speaking, whey protein is known as a naturally complete protein because it contains all of the essential amino acids required in the daily diet. It is also one of the richest sources of branched chain amino acids (BCAAs, in particular leucine) which play an important role in muscle protein synthesis. Moreover, some of the individual components of whey protein have been shown to prevent viral and bacterial infection and modulate immunity in animals. Whey protein is the preferred choice of proteins to treat persons suffering from sarcopenia, but is also suitable for healthy persons, such as sportsmen and active elderly.

As a source of whey protein to be used in the present invention, any commercially available whey protein source may be used, i.e. whey obtained by any process for the preparation of whey known in the art, as well as whey protein fractions prepared thereof, or the proteins that constitute the bulk of the whey proteins being β-lactoglobulin, α-lactalbumin and serum albumin, such as liquid whey, or whey in powder form, such as whey protein isolate (WPI) or whey protein concentrate (WPC). Whey protein concentrate is rich in whey proteins, but also contains other components such as fat, lactose and glycomacroprotein (GMP), a caseine-related non-globular protein. Typically, whey protein concentrate is produced by membrane filtration. On the other hand, whey protein isolate consists primarily of whey proteins with minimal amounts of fat and lactose. Whey protein isolate usually requires a more rigorous separation process such as a combination of microfiltration and ultrafiltration or ion exchange chromatography. It is generally understood that a whey protein isolate refers to a mixture in which at least 90 weight % of the solids are whey proteins. A whey protein concentrate is understood as having a percentage of whey proteins between the initial amount in the by-product (about 12 weight %) and a whey protein isolate. In particular, sweet whey, obtained as a by-product in the manufacturing of cheese, acid whey, obtained as a by-product in the manufacturing of acid casein, native whey, obtained by milk microfiltration or rennet whey, obtained as a by-product in the manufacturing of rennet casein, may be used alone or in combination as source of globular whey proteins.

Furthermore, whey proteins may originate from all kinds of mammalian animal species, such as, for instance cows, sheep, goats, horses, buffalo's, and camels. Preferably, the whey protein is of bovine origin.

Preferably, the whey protein source is available as a powder, preferably the whey protein source is a WPC or WPI.

Whey protein isolate consists mainly of a mixture of β-lactoglobulin (about 65 weight %), α-lactalbumin (about 25 weight %) and serum albumin (about 8 weight %). These proteins are globular proteins that are sensitive to aggregation in the denaturated state. The denaturation temperature of β-lactoglobulin is pH-dependent; at pH 6.7, irreversible denaturation occurs when the protein is heated at temperatures above 65° C. In the denaturated state, a free thiol group is exposed. This free thiol group can initiate inter-protein disulfide interactions leading to a polymerization reaction resulting in aggregate formation. Also two disulfide bridges, present in native β-lactoglobuline, are involved in the polymerization reaction and also other sulphur containing groups including cysteine residues are thought to play a role.

α-Lactalbumin also has a denaturation temperature of about 65° C. Since α-lactalbumin does not have a free thiol group (only four disulfide bridges), solutions of pure α-lactalbumin are not irreversibly denaturated under most processing conditions. However, in the presence of β-lactoglobulin, as is the case in e.g. a whey protein concentrate or isolate, α-lactalbumin is more sensitive to irreversible denaturation through the formation of α-lactalbumin/β-lactoglobulin complexes in which also disulfide bridges in β-lactoglobuline and α-lactalbumin are involved via interchange reactions. Also the circumstance that α-lactalbumin contains cystein residues is considered to contribute to a certain sensitivity to irreversible denaturation. Denaturated β-lactoglobulin and α-lactalbumin are both sensitive to calcium; this is particularly the case in the pH range of about 5 to about 8 where the protein carries a neutral to net negative charge. At pH 4, the protein carries a net positive charge and is less sensitive to calcium-induced aggregation.

The size, shape and density of the protein aggregates are influenced by a number of environmental and processing parameters including temperature, heating rate, pressure, shear, pH and ionic strength. Depending on the combination of these parameters, the aggregates may form a space-filling network (gel), fibrils or compact micro-particles. For example microparticulated whey can be formed under specific ionic strength and shear conditions. These particles have a compact structure, a high intrinsic viscosity and a low specific volume. Further, it is known that a relationship exists between aggregates size and heating temperature for microparticulated whey produced under shear conditions. Microparticulated whey protein has received a lot of interest lately for application as a fat replacer or viscosity enhancer for yoghurt.

One of the major problems encountered with the production of liquid ready-to-use compositions containing globular proteins in general, and whey proteins in particular, is their limited processability and heat-sensitivity. As these proteins are heated above their denaturation temperature in a sterilization process, they unfold and are transformed into a reactive state, polymerize into aggregates or gels. As a consequence, the heat-treated liquid composition exhibits unwanted sensorial attributes like chalkiness, sandiness, lumpiness. Besides, the shelf life of these products is limited in that sediment and/or cream layers are formed soon after production. In a composition with a high globular protein content, in particular whey, these instabilities are even more pronounced and result in products with an unwanted high viscosity and extensive fouling and blocking of the UHT heating equipment.

Surprisingly, the inventors have now found that it is possible to prepare a pasteurized or sterilized liquid enteral nutritional composition having a long shelf life by means of a method wherein a composition that comprises mainly globular proteins as a protein source, in particular whey proteins, is subjected to a specific heat-treatment that comprises the steps of converting the composition into an aerosol and quickly heating and cooling said aerosol to obtain a composition of unique heat-treated globular proteins, in particular whey proteins. Thus the present invention concerns a pasteurized or sterilized liquid enteral nutritional composition. Also the present invention concerns a method for the preparation of a pasteurized or sterilized liquid enteral nutritional composition, which comprises the method for the heat-treatment of non-hydrolysed globular proteins, in particular whey proteins, as described below.

Without being bound (or restricted) to any theory, it is believed that raising the temperature quickly to a temperature well above the denaturation temperature of the whey protein, leads to denaturation of whey protein. The thiol group of β-lactoglobulin, the main constituent of whey protein, is being exposed and termination reactions forming disulfide bridges dominate initially after heating. As a result, small, compact whey protein particles are formed which are largely inert in any further heat-treatment. On the contrary, in a heat-treatment just above the denaturation temperature of the whey, the aggregation reaction is limited by the rate of unfolding of the protein, leading to extensive polymerization and voluminous protein aggregates. Also, when the whey is heated to high temperatures (i.e. far above the protein denaturation temperature, for example at 110° C.) via a slow heating process, i.e. a process in which the temperature of the protein solution is raised gradually, for example 0.1 to 2° C. per second, using e.g. retort, plate or tubular heat exchangers, the whey exhibits extensive polymerization during heating up when process temperatures pass the temperature window just above the denaturation temperature of the whey protein. As a result, the product is too thick, lumpy, sandy and extensive fouling is observed in the heating apparatus.

Thus surprisingly, it was found that the time for whey proteins to be spent in a temperature window just above the denaturation temperature, should be minimized.

Method of Heat Treatment

The non-hydrolysed globular proteins, in particular whey proteins, are subjected to a heat-treatment, comprising the consecutive steps of:
a) adjusting the pH of an aqueous composition comprising non-hydrolysed globular proteins to a value of between about 2 and 8;
b) converting the composition comprising non-hydrolysed globular proteins obtained in step a) into an aerosol;
c) subjecting the aerosol obtained in step b) to a temperature of 100 to 190° C. during a time of about 30 to 300 milliseconds;
d) flash-cooling the heat-treated aerosol obtained in step c) to a temperature below 85° C. to obtain an aqueous solution comprising heat-treated globular proteins.

It is emphasized that the aqueous composition comprising non-hydrolysed globular proteins may contain, next to non-hydrolysed globular proteins, in particular whey, any other nutritional ingredients, such as other proteins, amino acids, fat, carbohydrates, fibers, minerals, vitamins, and the like, and that these ingredients may be present when subjecting the aqueous composition to the method according to the invention, in particular step b).

In one embodiment, the pH of the aqueous composition of non-hydrolysed globular proteins in step a)>3 and ≤8.

In one embodiment, the pH of the aqueous composition of non-hydrolysed globular proteins in step a) is about 2 to 5. More preferably, the pH of the aqueous composition of non-hydrolysed globular proteins in step a) is about 4.

In yet another embodiment, the pH of the aqueous composition of non-hydrolysed globular proteins in step a) is about 6 to 8. More preferably, the pH of the aqueous composition of non-hydrolysed globular proteins in step a) is about 7.

Preferably, said globular proteins are whey proteins.

In one embodiment in step c) the aerosol is subjected to a temperature of 100 to 190° C. during a time of at least 30, or about 40, about 50, about 60, about 70, about 80, about 90 or about 100 milliseconds to at most about 280, about 260, about 240, about 220, about 200, about 190, about 180, about 170, about 160 or about 150 milliseconds.

In one embodiment in step c) the aerosol is subjected to a temperature of at least about 110, about 120, about 130, about 140, about 150, about 160, about 170 or about 180° C.

In one embodiment, the aerosol obtained in step b) is subjected to a temperature of 110 to 180° C., during a time of about 30 to 200 milliseconds, more preferably 40 to 150 milliseconds, more preferably 80 to 120 milliseconds. In another embodiment, the aerosol obtained in step b) is subjected to a temperature of 110° C., during a time of about 30 to 200 milliseconds, more preferably 40 to 150 milliseconds, more preferably 80 to 120 milliseconds. In yet another embodiment, the aerosol obtained in step b) is subjected to a temperature of 170° C., during a time of about 30 to 200 milliseconds, more preferably 40 to 150 milliseconds, more preferably 80 to 120 milliseconds.

In one embodiment, in step a) the pH of an aqueous composition of non-hydrolysed whey proteins is adjusted to a value of about 4 (acid whey solution), and the aerosol obtained in step b) is subjected to a temperature of 110° C., during a time of about 30 to 200 milliseconds, more preferably 40 to 150 milliseconds, more preferably 80 to 120 milliseconds.

In another embodiment, in step a) the pH of an aqueous composition of non-hydrolysed whey proteins is adjusted to a value of about 7 (neutral whey solution), and the aerosol obtained in step b) is subjected to a temperature of 170° C., during a time of about 20 to 200 milliseconds, more preferably 40 to 150 milliseconds, more preferably 80 to 120 milliseconds.

In one embodiment, in step c), the conversion of the composition of non-hydrolysed globular proteins obtained in step a) into an aerosol is done using a spray nozzle, as described below in detail.

In one embodiment, step d) is performed by transporting the aerosol into a vacuum chamber (flash-cooling) to remove an amount of water by evaporation, equivalent to the amount of steam used and the product is cooled by indirect cooling to a temperature of less than about 85° C., preferably less than about 60° C. This method allows fast cooling and quick removal of volatiles (i.e. steam). The cooling preferably takes place nearly instantaneously, i.e. in a time window preferably of milliseconds. In one embodiment, the aqueous solution comprising heat-treated globular proteins obtained in step d) is comprised in the liquid nutritional composition according to the invention. Thus in one embodiment the aqueous solution comprising heat-treated globular proteins obtained in step d) comprises an amount of water equivalent to the amount of water obtained in step a).

It is without saying that any of the aforementioned preferred values (pH, temperature and time) and ranges thereof for each of the steps a), b), c) and d) may be combined in an intelligent manner, without departing from the scope of the invention.

A similar, albeit fundamentally differently operated method has been disclosed in EP 1 351 587 (Nutricia N.V, also published as US 2004/0057867). This document discloses a method for sterilization or pasteurization of heat-sensitive proteins such as whey protein. The method uses a spray-cooking apparatus, wherein a liquid product is subjected to superheated steam. The time of heating is less than 20 milliseconds. Such a period of time was found sufficient to kill microorganisms to a desired degree. The method described in this document is in particular designed to produce powders upon drying in a spray tower. This document does not disclose or suggest to collect a liquid aqueous nutritional composition. Although a similar apparatus was used in the examples of the present application, the apparatus was operated differently, a first major difference being that a liquid aqueous composition is obtained and a second essential difference being that the aerosol is subjected to heat for a longer time. According to the method of the present invention a longer duration of heating time is necessary. Apparently, sufficient time is required to allow the formation of small, compact whey proteins to take place, making it possible to produce sterilized or pasteurized liquid enteral nutritional compositions containing high concentrations of whey proteins.

Apparatus

The apparatus to carry out the invention may be selected by the skilled person based on the steps described above. Basically, the apparatus to carry out the invention comprises a nozzle for atomizing the composition (step b), a chamber to heat the aerosol (step c), and a chamber to cool the heated aerosol (step d). Preferably, the heating is done by mixing the aerosol with steam of a certain temperature (and at a certain steam pressure). When using steam, the apparatus may comprise a nozzle and a mixing chamber. A mixing chamber generally comprises one or more inflow openings for steam flows and for product flows, in which a product flow may optionally be premixed with a part of the steam. It may be preferable to select the mixing chamber such that only one product flow is atomized with one steam flow, since this simplifies the cleaning of the mixing chamber after use.

A schematic representation of a suitable nozzle for atomization according to the invention is shown in EP 1351587, FIG. 1, in which a nozzle with mixing chamber is shown. Said FIG. 1 is included herein by reference. It turns out that a nozzle with mixing chamber can be very effectively used for the heat treatment of a product. A suitable mixing chamber is generally characterized in that steam and atomized product to be treated are mixed, while the volume throughput of the steam will be much greater than that of the atomized product to be treated and the residence time of the atomized product is sufficiently to obtain the desired heat-treated globular protein. The volume ratio between the steam flow and the product flow may range between, for instance, about 20:1 and 150:1. It is important that the pressure in the mixing chamber is higher than in the space to which the atomized product is passed.

The form and size of the inflow openings for the steam flow (1) and the flow of the product in liquid form (2) in the mixing chamber and their mutual position are selected such that intensive mixing takes place between product and steam. It is noted that the inflow openings can be placed such that the steam flow and the product flow enter the mixing chamber in substantially parallel direction. This may take place in both a horizontally, vertically and diagonally manner. However, it is also possible that the steam flow and the product flow enter the mixing chamber at different angles, for instance a vertical steam flow and a horizontal product flow. The inflow openings are further arranged such that the product is atomized in small droplets, which after a short residence time in the mixing chamber (4) leave the mixing chamber through an outflow opening (5), for instance to a cooling chamber (6). The inflow opening(s) for the steam flow preferably contain a steam distribution plate (3). By changing the dimensions of the mixing chamber and/or the outflow opening(s) in the manner known to those skilled in the art, the average residence time and particle size of the atomized droplets can be varied. To set a suitable residence time in the mixing chamber is a simple matter of optimization for the skilled person and depends at least on the temperature and pressure in the mixing chamber.

The mixing is preferably realized by contacting the atomized product flow and the steam flow close to the inflow opening of the product in the mixing chamber and bringing the steam at high speed around the atomized product. In a preferred embodiment, such a mixing takes place by bringing the steam near the product concentrically around the inflow opening of atomized product in the mixing chamber.

The product flow to steam flow ratio can be varied in a ratio of 1.6 to 10 kg product in liquid form per kg steam. Very good results are realized at a wet product flow to steam flow ratio of 2.4 to 8 kg product in liquid form per kg steam.

In principle, any type of mixing chamber is suitable in which steam and product can be mixed and atomized. Very suitable for mixing and atomizing a product-steam mixture according to the invention is a nozzle such as "two-fluid" type nozzle, an example of which is described in EP 0438783, FIG. 1. This nozzle contains a small chamber at the end of a product line in which steam and product are combined. To increase the capacity, more nozzles can be used in a parallel arrangement.

The temperature of the supplied saturated or superheated steam in the method according to the invention is preferably in the range of 100 and 190° C., more preferably between 100 and 180° C., still more preferably between 100 and 170° C. In general, the temperature in the mixing chamber will be maintained at the desired level through the steam, although it is also possible that the mixing chamber itself is heated by another heat source.

Good results are obtained when introducing the steam into the mixing chamber at a steam pressure of 1.5 to 10 bar, and in particular at a steam pressure of 1.8 to 8.2 bar, in mixing chambers about 1 to 20 cm in length. This pressure is preferably measured just before the steam is introduced into the mixing chamber via a spray nozzle.

Preferably, the particle size (aggregate size) of the flash-cooled aerosol (obtained in step d) is less than about 30 μm, more preferably less than about 10 μm, still more preferably less than 5 μm, and most preferably less than 1 μm. At particle diameters above 30 μm, the nutritional composition may start to taste sandy, which is not favoured.

Depending on the temperature/time combination, the method according to the invention may not provide sufficient pasteurization or sterilization. For instance, 100 milliseconds at 110° C. does not provide sufficient microbial sterility for a neutral product. However, 100 milliseconds at 170° C. would provide sufficient sterility.

In one embodiment, the product obtained from step d) is further pasteurized using conventional equipment such as a plate or tubular heat exchanger, scraped surface heat exchanger or a retort to give the final product. Most excellent results are obtained when using a plate heat exchanger. The invention therefore also relates to the above described method according to the invention, comprising steps a), b), c) and d), subsequently comprising a pasteurization step using a plate heat exchanger. The plate heat exchanger is preferably operated at 92° C. for 30 seconds.

In another embodiment, a sterile product is obtained from step d) or from the above mentioned subsequent pasteurization step, which can be filled aseptically in aseptic containers in a further process step.

Nutritional Composition

Surprisingly, this invention makes it possible to produce a liquid enteral nutritional composition with a high content of non-hydrolysed globular protein, in particular whey protein, with a long shelf life and with a low viscosity.

In the context of this application, "non-hydrolysed" proteins is equivalent to "intact" proteins, meaning that the proteins have not been subjected to an hydrolysis process. However, minor amounts of hydrolysed proteins may be present in the source of non-hydrolysed proteins, or may be added to the formulation, such as additional amino acids, such as, for example leucine, isoleucine, and the like. In this context, "minor" should be understood as an amount of about 20 weight % or less, for example of about 10 weight % or less. The term "about" should be interpreted as a deviation of plus or minus 10% of the given value.

Hence, in an embodiment of the invention, a liquid enteral nutritional composition comprising 10 to 20 g of non-hydrolysed globular proteins per 100 ml of the composition is provided.

Also, in an embodiment of the invention, a liquid enteral nutritional composition having a pH>3 and ≤8 comprising 9 to 20 g of non-hydrolysed globular proteins per 100 ml of the composition is provided.

Also, in an embodiment of the invention, a liquid enteral nutritional composition comprising 9 to 20 g of non-hydrolysed globular protein per 100 ml of the composition is provided, with the proviso that a UHT-sterilized composition comprising 9.2 weight % whey protein having a pH=3 is excluded.

Preferably, the globular proteins are whey proteins. In another embodiment, the amount of non-hydrolysed globular proteins is 9, 10, 11, 12, 13, 14, 15, 16, 17, 18, 19 or 20 gram per 100 ml of the composition, or any value in between the aforementioned values.

In one embodiment, the pH of the liquid enteral nutritional composition is about 2 to about 8. In one embodiment, the pH of the liquid enteral nutritional composition is >3 and ≤8. In another embodiment, the pH is about 2, 3, 4, 5, 6, 7, or 8 or any value in between the aforementioned values.

In a specific embodiment of the composition according to the invention, the composition is acidic (yoghurt-like or juice-like) with a pH of about 4. Acidification may be achieved by any method known to the skilled person, such as the addition of an acid (such as, for instance lactic acid, citric acid, phosphoric acid) or through fermentation. The thus obtained composition has a pleasant mild acidic taste which can be flavoured perfectly with a fruity flavour.

In a further specific embodiment of the invention, the composition has a neutral pH (i.e. a pH of about 7). The thus obtained composition has a pleasant taste which may optionally be flavoured with e.g. vanilla, chocolate, caramel, banana, strawberry.

According to another embodiment of the present invention, the protein provides 10% to 50%, preferably at least 15%, more preferably at least 20%, at least 25%, at least 30% of the total energy content of the composition. The % of total energy is also abbreviated as En %; En % is thus short for energy percentage and represents the relative amount that a constituent contributes to the total caloric value of the composition. The high levels of protein are beneficial for patients who may not be physically capable of receiving a large volume, for example, fluid restricted patients. Such patients can be given a reduced level of fluid while still receiving a required amount of nutritional support per day.

In the context of this application, the term "at least" also includes the starting point of the open range. For example, an amount of "at least 95 weight %" means any amount equal to 95 weight % or above.

In one embodiment of the present invention, the composition has an energy density of at least 0.36 kcal/ml, preferably at least 1.0 kcal/ml, preferably at least 1.5 kcal/ml, preferably at least 2.0 kcal/ml, more preferably at least 2.4 kcal/ml. Although the composition has a high energy density, it also has a sufficiently low viscosity to allow it to be consumed by persons that may have difficulty swallowing products or those that are tube fed.

In one embodiment of the present invention, the amount of whey proteins in the liquid nutritional composition according to the invention is at least 85 weight %, more preferably at least 90 weight %, more preferably at least 95 weight % of the total protein present in the liquid nutritional composition.

In a further embodiment of the present invention, the composition may comprise up to about 40 weight % of a non-globular protein, such as casein, caseinate, micellar casein isolate and the like, and any mixture thereof, preferably less than or equal to 20 weight %, more preferably less than or equal to 10 weight % of the total protein present in the liquid nutritional composition.

In one embodiment of the present invention, the composition may comprise a free amino acid, or a mixture of free amino acids, up to 5 g/100 ml, more preferably less than 2 g/100 ml, more preferably less than 1 g/100 ml, most preferably less than 0.5 g/100 ml The composition according to the invention is designed to either supplement a person's diet or to provide complete nutritional support. Hence, the composition according to the invention may further comprise at least fat and/or carbohydrate and/or a source of vitamins and minerals and/or a source of prebiotics. Preferably, the composition according the invention is a nutritionally complete composition.

Fat

In one embodiment of the present invention, the liquid nutritional composition according to the invention further comprises fat, said fat providing between 20 to 40% of the total energy content of the composition. For a 1.6 kcal/ml composition, this amounts to 32 to 64 kcal per 100 ml. For a 2.4 kcal/ml composition, this amounts to 48 to 96 kcal per 100 ml.

The fat may include medium chain triglycerides (MCT, mainly 8 to 10 carbon atoms long), long chain triglycerides (LCT) or any combination of the two types. MCTs are beneficial because they are easily absorbed and metabolized in a metabolically-stressed patient. Moreover, the use of MCTs will reduce the risk of nutrient malabsorption. LCT sources, such as canola oil, rapeseed oil, or corn oil are preferred because they can reduce immune suppression associated with certain types of fatty acids concentrated in the body.

Preferably, the fat comprises 30 to 60 weight % of animal or algal fat, 40 to 70 weight % of vegetable fat and optionally 0 to 20 weight % of MCTs based on total fat of the composition. The animal fat preferably comprises a low amount of milk fat, i.e. lower than 6 weight %, especially lower than 3 weight %. In particular, a mixture of corn oil, egg oil, and/or canola oil and specific amounts of marine oil are used. Egg oils, fish oils and algal oils are a preferred source of non-vegetable fats. Especially for compositions that are to be consumed orally, in order to prevent formation of off-flavours and to decrease a fishy after-taste, it is recommended to select ingredients that are relatively low in docosahexanoic acid (DHA), i.e. less than 6 weight %, preferably less than 4 weight % of the fat. Marine oils containing DHA are preferably present in the composition according to the invention in an amount lower than 25 weight %, preferably lower than 15 weight % of the fat. On the other hand, inclusion of eicosapentanoic acid (EPA) is highly desirable for obtaining the maximum health effect. The amount of EPA ranges preferably between 4 weight % and 15 weight %, more preferably between 8 weight % and 13 weight % of the fat. The weight ratio EPA:DHA is advantageously at least 6:4, for example between 2:1 and 10:1.

Also, the liquid nutritional composition according to the invention may beneficially comprise an emulsifier. Commonly known emulsifiers may be used, such as lecithin, and generally the emulsifier contributes to the energy content of the fat in said composition.

Carbohydrates

In one embodiment of the present invention, the liquid nutritional composition according to the invention further comprises carbohydrate, said carbohydrate providing between 30 to 60% of the total energy content of the composition. Preferably, the carbohydrate provides at least 40% of the total energy content of the composition according to the invention.

The composition of the carbohydrate preferably is such that high viscosities, excessive sweetness, excessive browning (Maillard reactions) and excessive osmolarities are avoided. Acceptable viscosities and osmolarities may be achieved by adjusting the average chain length (average degree of polymerisation, DP) of the carbohydrates between 1.5 and 6, preferably between 1.8 and 4. In order to avoid excessive sweetness, the total level of sucrose and fructose is less than 52% and preferably less than 40% of the weight of the carbohydrate, especially of the digestible carbohydrate. Long-chain digestible carbohydrates such as starch, starch fractions and mild starch hydrolysates (DP≥6, DE<20), may also be present, preferably in an amount of less than 25 weight %, especially less than 15 weight % of the carbohydrate, and less than 6 g/100 ml, preferably less than 4 g/100 ml of the total liquid enteral composition according to the invention.

In one embodiment of the present invention, the carbohydrate includes maltodextrose with a high DE (dextrose equivalent). In one embodiment the carbohydrate includes maltodextrose with a DE of >20, preferably >30 or even >40, such as a DE of about 47. In one embodiment of the present invention, the carbohydrate includes maltodextrose with a high DE in an amount of at least 35 weight %, preferably at least 50 weight %, preferably at least 65 weight %, preferably at least 90 weight % of the total weight of carbohydrate. In one embodiment of the present invention, the carbohydrate includes maltodextrose with a low DE of 2 to 20. In one embodiment of the present invention, the carbohydrate includes maltodextrose with a low DE of 2 to 10, preferably with a low DE of about 2. In one embodiment of the present invention, the carbohydrate includes maltodextrose with a low DE in an amount of less than 35 weight %, preferably less than 20 weight %, preferably less than 10 weight % of the carbohydrate. Maltodextrose with a low DE may also be referred to as maltodextrine. In another embodiment of the present invention, the carbohydrate includes maltodextrose with a high DE, preferably a DE of >20, preferably >30 or even >40, most preferably a DE of about 47 in combination with maltodextrose with a low DE, preferably a low DE of 2 to 20, more preferably a low DE of 2 to 10, most preferably with a low DE of about 2. As is known, maltodextrose with a low DE, such as of about 2, gives rise to a high viscosity. Maltodextrose with a high DE, such as of about 47 gives rise to a low viscosity, but is very sweet. The combination of both maltodextroses optimizes the balance between sweetness and viscosity. In one embodiment of the present invention, the carbohydrate includes at least 65 weight %, preferably at least 90 weight %, based on total weight of carbohydrate of maltodextrose with a DE>40, preferably with a DE of about 47 and 0 to 10 weight % of maltodextrose with a DE 2 to 10, preferably with a DE of about 2.

In another embodiment of the present invention, the carbohydrate includes trehalose. As was indicated, it is one of the main objects of the invention to provide a nutritional composition with a low viscosity. Sucrose is very well suited for such purpose, but gives rise to very sweet compositions, which are in general disliked by the consumer. Maltodextrose with a low DE, such as of about 2, does not suffer from the latter drawback, but gives rise to a high viscosity. Maltodextrose with a high DE, such as of about 47 gives rise to a low viscosity, but is again very sweet, and gives further rise to the undesired Maillard reactions. Trehalose is a preferred choice of carbohydrate, as it gives rise to a low viscosity, no undesired Maillard reactions and it has a sweetness about half of that of sucrose. In one embodiment of the present invention, the carbohydrate includes trehalose in an amount of 20% to 60% of the weight of the carbohydrate, in an amount of 20% to 45%, more preferably in an amount of 25% to 45% of the weight of the carbohydrate.

Vitamins and Minerals

The composition according to the invention may contain a variety of vitamins and minerals. Overall, the composition according to the invention preferably includes at least 100% of the United States Recommended Daily Allowance (USRDA) of vitamins and minerals in a one liter portion.

In one embodiment of the present invention, the composition according to the invention provides all necessary vitamins and minerals. For example, the composition according to the invention preferably provides 6 mg of zinc per 100 ml of the composition which is beneficial for tissue repair in a healing patient. Preferably, the composition according to the invention (also) provides 25 mg of vitamin C per 100 ml of the composition to aid patients with more severe healing requirements. Further, preferably, the composition according to the invention (also) provides 2.25 mg iron per 100 ml of the composition. Iron is beneficial in maintaining bodily fluids as well as circulatory system functions in an elderly patient.

In another embodiment of the present invention, the amount of divalent ions ranges between 170 mg/100 ml and 300 mg/100 ml and preferably between 180 mg/100 ml and 280 mg/100 ml. Preferably, the amount of calcium ranges between 155 mg/100 ml and 300 mg/100 ml and preferably between 190 mg/100 ml and 250 mg/100 ml. The phosphorus content can be above 10 mg per g of protein, with a calcium to phosphorus weight ratio between 1.0 and 2.0, preferably between 1.1 and 1.7. Carnitin may advantageously be present in an amount of 8 mg/100 ml to 1000 mg/100 ml, preferably 10 mg/100 ml to 100 mg/100 ml of composition; it may have the form of carnitin, alkyl carnitin, acyl carnation or mixtures thereof. Organic acids are preferably present at a level of between 0.1 g/100 ml to 6 g/100 ml, especially 0.25 g/100 ml to 3 g/100 ml. These acids include short fatty acids such as acetic acid, hydroxy acids such as lactic acid, gluconic acid, and preferably polyvalent hydroxy acids, such as malic acid and citric acid. In one embodiment of the present invention, the present composition also comprises citric acid.

Prebiotics

The liquid enteral nutritional composition according to the invention may be fortified with a prebiotic, for example, with non-digestible carbohydrates (dietary fibres), such as fructo-oligosaccharides and/or inulin. In an embodiment, the composition according to the invention comprises 0.5 g/100 ml to 6 g/100 ml of non-digestible carbohydrates. Herein non-digestible carbohydrates are also referred to as dietary fibres. The dietary fibres include non-digestible oligosaccharides having a DP of 2 to 20, preferably 2 to 10. More preferably, these oligosaccharides do not contain substantial amounts (less than 5 weight %) of saccharides outside these DP ranges, and they are soluble. These oligosaccharides may comprise fructo-oligosaccharides (FOS), trans-galacto-oligosaccharides (TOS), xylo-oligosaccharides (XOS), soy oligosaccharides, and the like. Optionally, also higher molecular weight compounds such as inulin, cellulose, resistant starch and the like may be incorporated in the composition according to the invention. The amount of insoluble dietary fibre such as cellulose is preferably lower than 20 weight % of the dietary fibre fraction of the composition according to the invention, and/or below 0.4 g/100 ml. The amount of thickening polysaccharides such as carrageenans, xanthans, pectins, galactomannans and other high molecular weight (DP>50) indigestible polysaccharides is preferably low, i.e. less than 20% of the weight of the dietary fibre fraction, or less than 1 g/100 ml. Instead, hydrolysed polysaccharides such as hydrolysed pectins and galactomannans can advantageously be included.

A preferred dietary fibre component is an indigestible oligosaccharide with a chain length (DP) of 2 to 10, for example Fibersol® (resistant oligoglucose), in particular hydrogenated Fibersol®, or a mixture of oligosaccharides having a DP of 2 to 10, such as fructo-oligosaccharides or galacto-oligosaccharides, which may also contain a small amount of higher saccharides (e.g. with a DP of 11 to 20). Such oligosaccharides preferably comprise 50 weight % to 90 weight % of the fibre fraction, or 0.5 g/100 ml to 3 g/100 ml of the composition according to the invention. Other suitable fibre components include saccharides that have only partial digestibility.

Viscosity

In one embodiment of the present invention, the viscosity of the liquid enteral nutritional composition is lower than 500 mPa·s, measured at 20° C. (i.e. room temperature) at a shear rate of 100 s$^{-1}$, preferably between 10 and 200 mPa·s, more preferably between 10 and 100 mPa·s, most preferably below 50 mPa·s. The viscosity may suitably be determined using a rotational viscosity meter using a cone/plate geometry. This viscosity is ideal for orally administering the liquid enteral nutritional composition according to the invention because a person may easily consume a serving having a low viscosity such as that displayed by the present invention. This viscosity is also ideal for unit dosages that are tube fed.

In one embodiment of the present invention, the density of the composition ranges between 1.00 g/ml and 1.20 g/ml, especially between 1.10 g/ml and 1.18 g/ml.

Dosage Unit

The liquid enteral nutritional composition according to the invention may have the form of a complete food, i.e. it can meet all nutritional needs of the user. As such, it preferably contains 1200 to 2500 kcal per daily dosage. The daily dosage amounts are given with respect to a daily energy supply of 2000 kcal to a healthy adult having a body weight of 70 kg. For persons of different condition and different body weight, the levels should be adapted accordingly. It is understood that the average daily energy intake preferably is about 2000 kcal. The complete food can be in the form of multiple dosage units, e.g. from 4 (250 ml/unit) to 20 units (50 ml/unit) per day for an energy supply of 2000 kcal/day using a liquid enteral nutritional composition according to the invention of 2.0 kcal/ml.

The liquid enteral nutritional composition can also be a food supplement, for example to be used in addition to a non-medical food. Preferably as a supplement, the liquid enteral nutritional composition contains per daily dosage less than 1500 kcal, in particular as a supplement, the liquid enteral nutritional composition contains 400 to 1000 kcal per daily dose. The food supplement can be in the form of multiple dosage units, e.g. from 2 (250 ml/unit) to 10 units (50 ml/unit) per day for an energy supply of 1000 kcal/day using a liquid enteral nutritional composition according to the invention.

In one embodiment of the present invention, a unit dosage comprises any amount of the liquid enteral nutritional composition according to the invention between 10 ml and 250 ml, the end values of this range included, preferably any amount between 25 ml and 200 ml, the end values of this range included, more preferably any amount between 50 ml and 150 ml, the end values of this range included, most preferably about 125 ml. For example, a person receiving 50 ml unit dosages can be given 10 unit dosages per day to provide nutritional support using a liquid enteral nutritional composition according to the invention of 2.0 kcal/ml. Alternatively a person receiving 125 ml unit dosages can be given 4 or 5 or 6 or 7 or 8 unit dosages per day to provide nutritional support using a liquid enteral nutritional composition according to the invention. Such small dosage units are preferred because of better compliance.

In one embodiment of the present invention, the composition is provided in a ready to use liquid form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the liquid nutritional enteral composition according to the present invention. In one embodiment of the present invention, the present liquid nutritional enteral composition may thus be obtained by dissolving or reconstituting a powder, preferably in an aqueous composition, in particular water.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of liquid (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

Preparation

Figure 1:
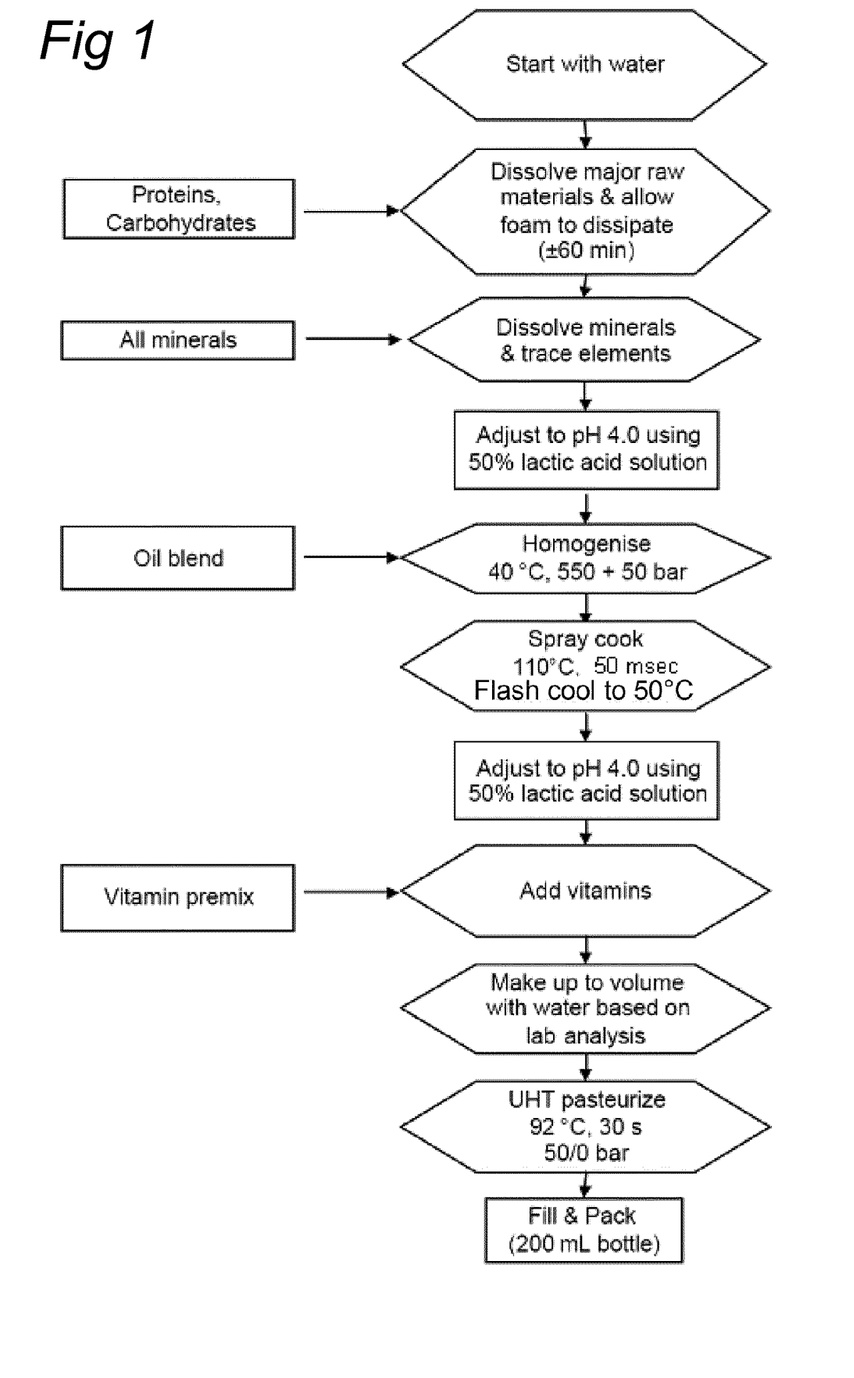
FIG. 1: Flow chart of a process for the manufacture of an acidic protein formula (12 g/100 ml) based on non-hydrolysed whey protein, according to the invention (Example 1 and Example 2).

The liquid enteral nutritional composition according to the invention may be prepared by the method as outlined in FIG. 1. Basically, the whey protein, carbohydrates and minerals are dispersed into water and the pH is adjusted using a suitable acid, such as lactic acid, citric acid, phosphoric acid and the like. The fat is blended into the product and this pre-emulsion is homogenized. This aqueous emulsion is subsequently atomized using the method of the invention, flash-cooled and collected. Optionally, the final pH and dry matter of the emulsion may be adjusted. The resulting product is subsequently pasteurized or sterilized using the known methods, such as, UHT processes and filled into containers or pasteurized or sterilized in containers in a retort. The liquid enteral nutritional composition according to the invention may alternatively be prepared by the method as outlined in FIG. 7. Basically, the whey protein, carbohydrates and minerals are dispersed into water and the pH is adjusted using a suitable acid or base. The fat is blended into the product and this pre-emulsion is homogenized. This aqueous emulsion is subsequently atomized, flash-cooled and collected in an aseptic tank from which it can be filled into aseptic containers.

Effectivity

The present invention is also directed at the nutritional composition according to the present invention for providing nutrition to a person in need thereof. The present invention also concerns a method of providing nutrition to a person in need thereof, comprising the steps of administering to said person the nutritional composition according to the present invention. Said person may be an elderly person, a person that is in a disease state, a person that is recovering from a disease state, or a person that is malnourished. Said person may also be a healthy person, such as a sportsman or active elderly. In other words, the present invention concerns the use of the nutritional composition according to the present invention in the manufacture of a composition for providing nutrition to a person in need thereof, preferably to an elderly person, a person that is in a disease state, a person that is recovering from a disease state, a person that is malnourished or a healthy person, such as a sportsman or active elderly. In a further aspect, the present invention relates to the non-hydrolysed heat-treated globular protein per se obtainable by the process according to the invention, and any product, formulation or composition comprising said heat-treated globular proteins, in particular whey proteins, in any form, such as a solution, suspension, dispersion, nutritional composition, medicament, or powder, in any concentration conceivable.

The invention will now be further elucidated by several examples, without being limited thereby.

EXAMPLES

A number of compositions were manufactured using the method according to the invention. These are summarized in Table 1.

TABLE 1

| Component | Nutritional composition | | | | |
| --- | --- | --- | --- | --- | --- |
|  | A1 | A2 | A3 | A4 | A5 |
| Energy value (kcal/ml) | 1.6 | 1.6 | 2.4 | 2.4 | 0.75 |
| Protein | WPC | WPI | WPI | WPI | WPI |
| (g/100 ml) | 12 | 12 | 16 | 16 | 12 |
| (En %) | 30 | 30 | 27 | 27 | 58 |
| Fat |  |  |  |  |  |
| (g/100 ml) | 4.4 | 4.4 | 8.5 | 8.5 | 0.75 |
| (En %) | 25 | 25 | 31 | 31 | 9 |
| Carbohydrates |  |  |  |  |  |
| (g/100 ml) | 18 | 18 | 25 | 25 | 5 |
| (En %) | 45 | 45 | 42 | 42 | 27 |
| Dietary fibre | 1.2 | 1.2 | 0 | 0 | 1.2 |
| Vitamins and Minerals | % of RDI | % of RDI | % of RDI | % of RDI | % of RDI |
| Final pH | 4.0 | 4.0 | 4.1 | 7.5 | 4.0 |

Example 1

Acidic Whey Protein Composition (12 g/100 ml) (Composition A1)

Figure 2:
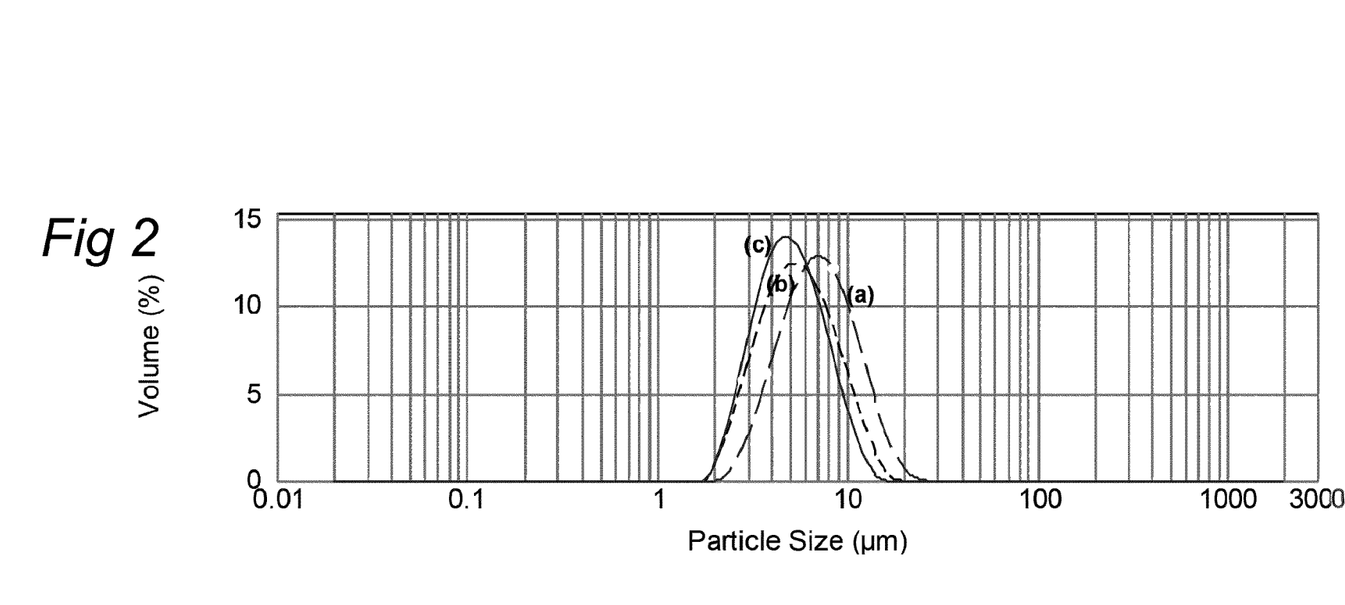
FIG. 2: Particle size distribution of the formulation of Example 1, processed according to the flow chart of FIG. 1, as measured with a Malvern Mastersizer 2000.
(a): product after homogenization at 30° C. and a pressure of 550/50 bar;
(b): product after spray-cooking at 110° C. for approximately 50 ms;
(c): product after UHT-pasteurization at 92° C. for 30 sec using a plate heat exchanger. The product is liquid with a viscosity of 150 mPa·s at a shear rate of 100 s$^{-1}$; the product has a smooth mouth feel.

A flow chart of the process is shown in FIG. 1. The protein (WPC powder of Lactalis, Prolacta 80), carbohydrates and minerals were dispersed in water and the solution was set to pH 4.0 using 50% lactic acid. The oil was blended into the product and the pre-emulsion was homogenised at 40° C. in a 2-stage homogenizer at a pressure of 550/50 bar. The product was then atomised into the spray-cooking chamber and instantly heated to 110° C. by mixing with steam and held at this temperature for approximately 50 msec. Subsequently, the product was flash-cooled to 50° C. and pumped into a holding tank. The final pH of the product was adjusted to pH 4.0 and the product was then UHT pasteurized at 92° C. for 30 sec and filled into 200 ml bottles. The product was liquid, with a viscosity of 150 mPa·s at 20° C. at a shear rate of 100 s$^{-1}$. The product had a smooth mouth feel. This is confirmed by the particle size distribution (FIG. 2), which shows that the spray-cooking has little effect on the particle size. Moreover, the spray-cooking step appears to have stabilised the protein aggregates against further aggregation: the particle size after UHT pasteurization is nearly unchanged compared to the spray cooked intermediate product. The average particle diameter as obtained from static light scattering (Malvern Mastersizer 2000), d[4,3], after homogenisation (a), spray-cooking (b) and UHT pasteurization (c) were 7.7 µm, 6.0 µm and 5.4 µm, respectively.

Example 2

Acidic Whey Protein Composition (12 g/100 ml) (Composition A2)

A recipe with composition A2 was made according to the process of Example 1. WPI powder from Fonterra (LGI 895) was used as the protein source. The final product was liquid, with a very low viscosity of 15 mPa·s at a shear rate of 100 s$^{-1}$. The product had a smooth mouth feel. The average particle diameter as obtained from static light scattering (Malvern Mastersizer 2000), d[4,3], after UHT pasteurization was 5.7 µm. Composition A5 was made in a similar way as composition A2.

Example 3

Acidic Whey Protein Composition (16 g/100 ml) (Composition A3)

Figure 4:
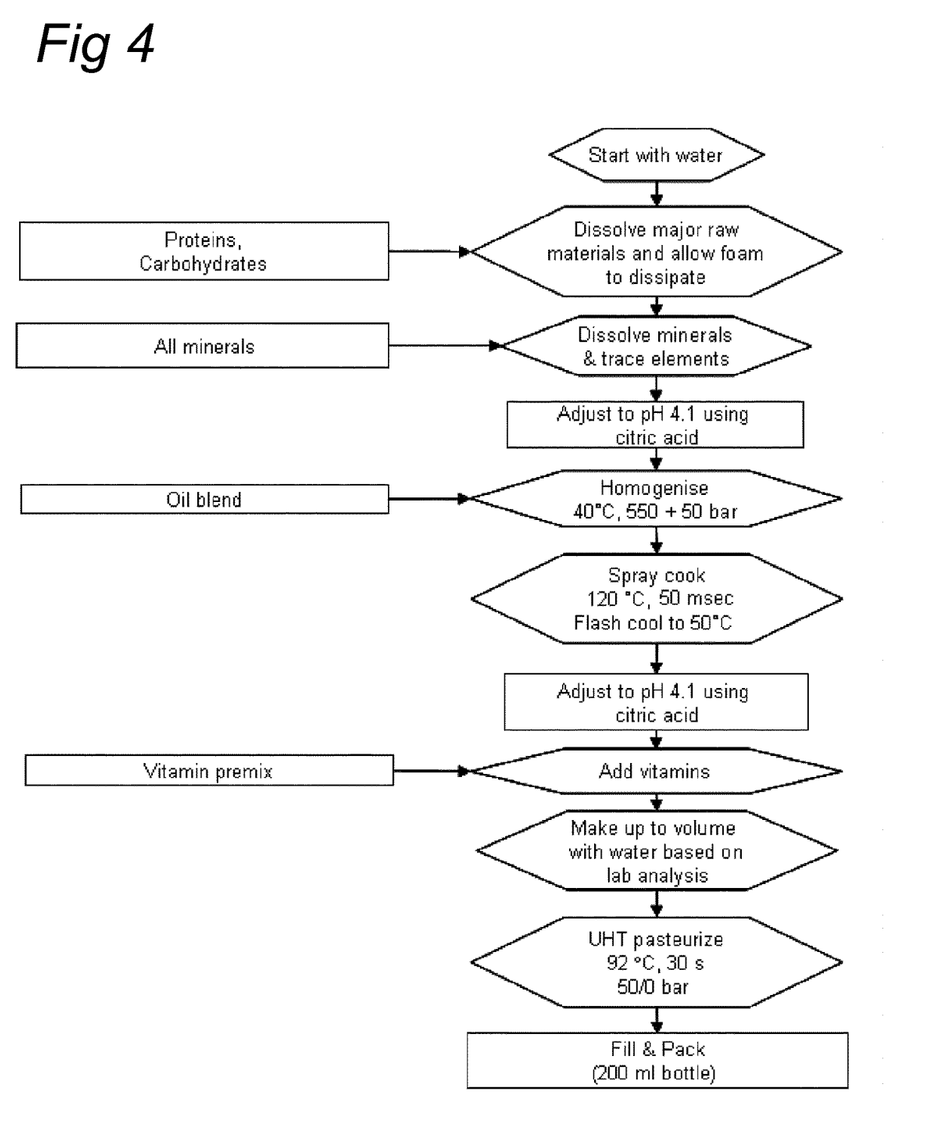
FIG. 4: Flow chart of a process for the manufacture of an acidic protein formula (16 g/100 ml) based on non-hydrolysed whey protein, according to the invention (Example 3).
Figure 5:
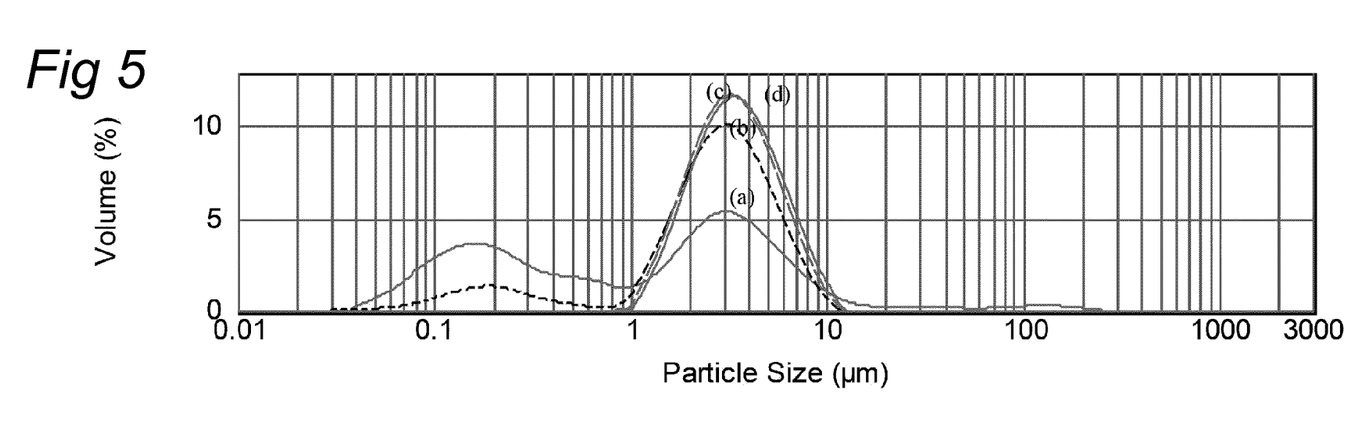
FIG. 5: Particle size distribution of the formulation of Example 3, processed according to the flow chart of FIG. 4, as measured with a Malvern Mastersizer 2000.
(a): product after homogenization at 30° C. and a pressure of 550/50 bar but before spray-cooking;
(b): product after spray-cooking at 120° C. for approximately 50 ms;
(c): product after UHT-pasteurization at 92° C. for 30 sec using a plate heat exchanger.
(d): product after retort-pasteurization at 92° C. for 30 sec.

A flow chart of the process is shown in FIG. 4. The protein (WPI) (Bipro®, Davisco), carbohydrates and minerals were dispersed in water and the solution was set to pH 4.1 using citric acid. The oil was blended into the product and the pre-emulsion was homogenised at 40° C. in a 2-stage homogenizer at a pressure of 550/50 bar. The product was then atomised into the spray-cooking chamber and instantly heated to 120° C. by mixing with steam and held at this temperature for approximately 50 msec. Subsequently, the product was flash-cooled to 50° C. and pumped into a holding tank. The final pH of the product was adjusted to pH 4.1 and the product was split in two batches. One batch was then UHT pasteurized at 92° C. for 30 sec and filled aseptically into aseptic 200 ml bottles. The product was liquid, with a viscosity of 75 mPa·s at a shear rate of 100 s$^{-1}$. The other batch was retorted (15 minutes at 92° C.). This product was liquid with a viscosity of 162 mPa·s at a shear rate of 100 s$^{-1}$ Both products had a smooth mouth feel. This is confirmed by the particle size distribution (FIG. 5), which shows that the spray-cooking has little effect on the particle size. Moreover, the spray-cooking step appears to have stabilised the protein aggregates against further aggregation: the particle size after UHT and retort pasteurization is nearly unchanged compared to the spray-cooked intermediate product. The average particle diameter as obtained from static light scattering (Malvern Mastersizer 2000), d[4,3], after homogenisation (a), spray-cooking (b) and UHT pasteurization (c) or retorting (d) were 4.7 µm, 3.7 µm, 3.9 µm or 3.8, respectively. It was observed that the mineral levels had only small effects on the final product characteristics like particle size, viscosity and shelf life stability.

Figure 6:
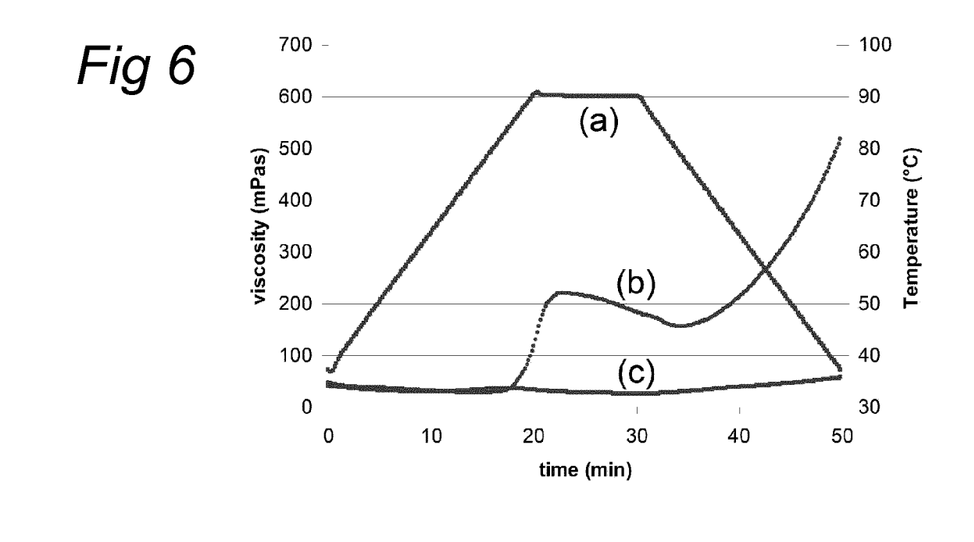
FIG. 6: Viscosity of spray-cooked and non spray-cooked samples of Example 3 when subjected to a temperature/time profile where:
Curve a) is the temperature/time profile;
Curve b) is the viscosity versus time for a non spray-cooked sample;
Curve c) is the viscosity versus time for a spray-cooked sample.
The left Y-axis refers to the viscosity, the right Y-axis to the temperature. Time is plotted on the x-axis.

In order to illustrate the effect of protein stabilization during spray-cooking, non spray-cooked and spray-cooked emulsions were subjected to the same heat treatment in a rheometer. Samples were heated up to 90° C., kept at 90° for 10 minutes and cooled back while measuring the viscosity. The temperature versus time curve is given in FIG. 6, curve (a). As can be seen, the non spray-cooked emulsion (b) shows a large jump in viscosity when the temperature exceeds 80° C., while the viscosity of the spray-cooked emulsion (c) largely stays unaffected, illustrating the stabilizing effect of the method according to the invention.

Example 4

Neutral Whey Protein Composition (16 g/100 ml) (Composition A4)

Figure 7:
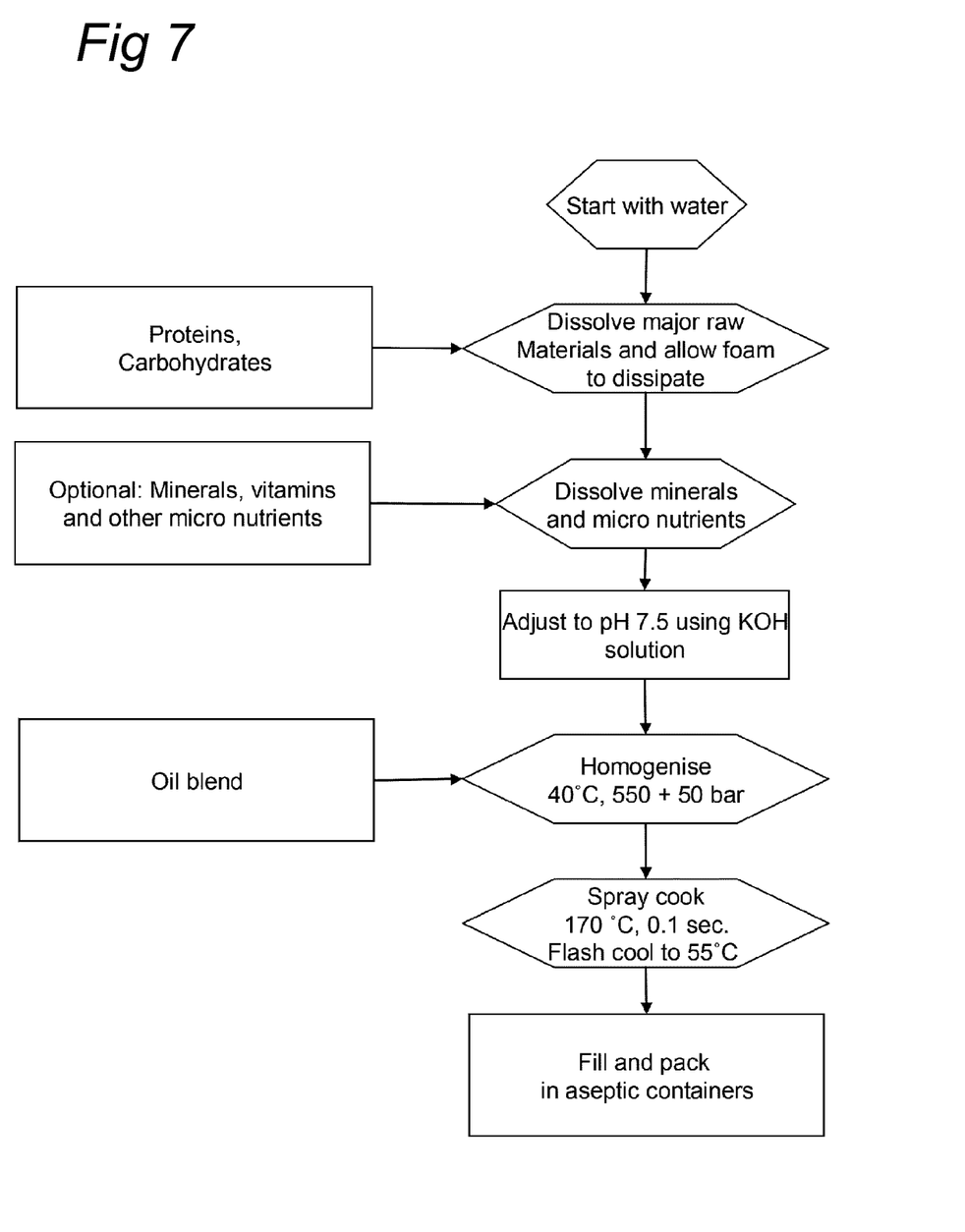
FIG. 7: Flow chart of a process for the manufacture of a neutral protein formula (16 g/100 ml) based on whey protein (Example 4).

A flow chart of the process is shown in FIG. 7. The whey protein isolate (WPI) (Bipro®, Davisco) and sucrose were dispersed in demineralised water and the solution was adjusted to pH 7.5 using a 10% KOH solution. Oil was blended into the product and the pre-emulsion was homogenised at 40° C. in a 2-stage homogenizer at a pressure of 550/50 bar. The product was then atomised into the spray-cooking chamber and instantly heated to 170° C. by mixing with steam and held at this temperature for approximately 100 ms. Subsequently, the product was flash-cooled to 55° C. and aseptically filled into aseptic 200 ml bottles. The product was liquid, with a viscosity of 97 mPa·s at a shear rate of 100 s$^{-1}$. The product had a smooth mouth feel. This is confirmed by the particle size distribution which shows that the spray-cooking has little effect on the particle size. If anything, the particles become smaller during the process. The average particle diameter as obtained from static light scattering (Malvern Mastersizer 2000), d[4,3], after homogenisation (a), spray-cooking (b) were 0.48 µm and 0.29 µm, respectively.

Example 5

Comparative Examples

The method according to the invention is compared with several other methods commonly employed in the field of nutritional compositions using the ingredients of composition A1. A summary is given in Table 2. Yoghurt like products with a pH less than pH 4.2 require a pasteurization step (either 90° C., 15 min or 92° C., 30 sec) for long shelf life products. The temperature required for pasteurization is well above the denaturation temperature of whey proteins. Denatured whey proteins are reactive molecules capable of aggregate formation. In the experiments we have observed that the same formulation can form a gel or a liquid product depending on the heating conditions. For example, slow heating in a rheometer, tube heat exchanger, or during gentle mixing in the retort results in a gelled product. However, when the product is heated under high shear in the surface scraped heat exchanger or heated instantaneously to above the denaturation temperature (as in the spray-cooking technique), a liquid products result.

Figure 3:
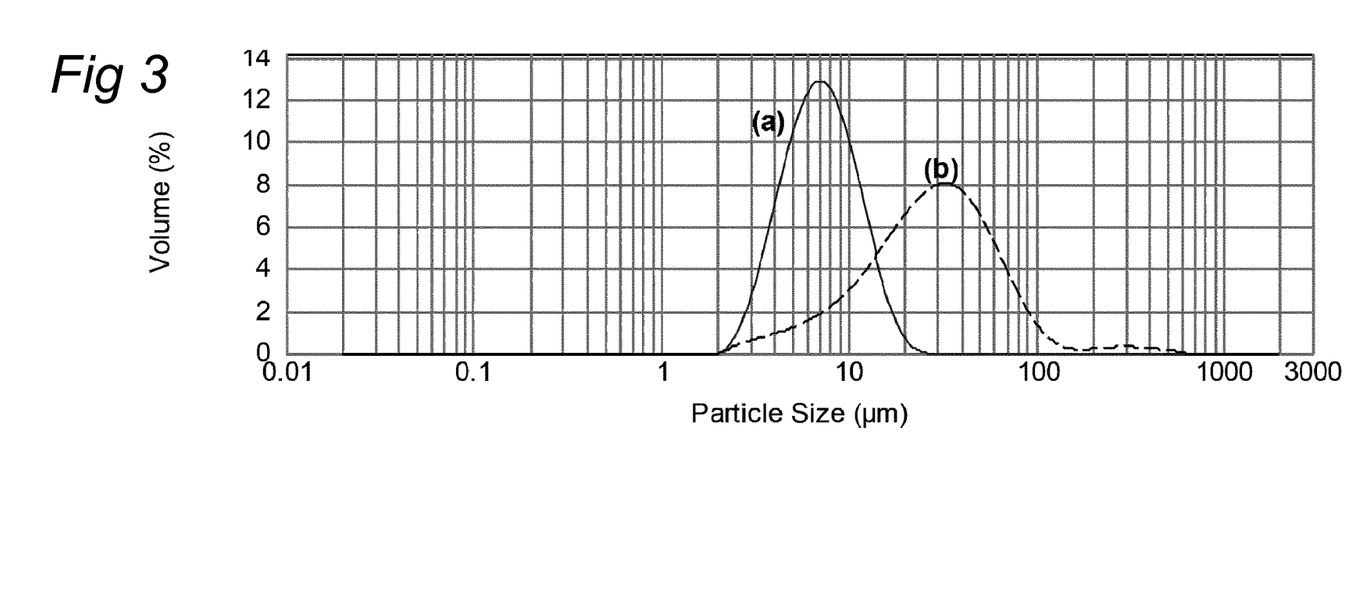
FIG. 3: Particle size distribution of the formulation of Example 1, processed with a Scraped Surface Heat Exchanger (SSHE), as measured with a Malvern Mastersizer 2000.
(a): particle size distribution before SSHE processing.
(b): particle size distribution after SSHE processing.

From Table 2, it can be observed that in the case of products that are retort-pasteurized or pasteurized in a tube or plate heat exchanger at a temperature of 80° C. for 30 seconds, large protein aggregates form, leading to gel formation and clogging of the processing equipment. It was not possible to process the composition A1, A2 or A3 using this technique. We also attempted to process composition A1 using a surface scraped heat exchanger (SSHE). This technique resulted in a liquid formulation; however the product had an extremely sandy mouth feel, likely due to the formation of large aggregates. This is confirmed by comparing the particle size distribution of the product (FIG. 3). The average particle size, d[4,3], increases from 7.7 μm (a) to 38 μm (b) as a result of the SSHE processing. However, it is interesting to note that the aggregates did not agglomerate to form a gel, suggesting that high shear enabled the formation of inert, but aggregated proteins having a large and undesirable size.

TABLE 2

| Exp | Homogenization Temp. | First heat-treatment | Pasteurization | Rating | Remarks |
|---|---|---|---|---|---|
| Comp. Ex 1 | 20° C. | None | retort 15 min at 90° C. | -- | The products gelled during retort sterilization |
| Comp. Ex 2 | 60° C. | Tube or plate heat exchanger 30 sec at 80° C. | retort 15 min at 90° C. | -- | Inline gelation of product during first heat treatment step |
| Comp. Ex 3 | 30° C. | Tube heat exchanger 30 sec at 30° C. | SSHE 2 min at 92° C. | 0 | Liquid product, but very sandy |
| Exp E1 | 40° C. | Spray-cooking according to the invention 50 msec at 110° C. | retort 15 min at 90° C. | + | Liquid product with ~400 mPa · s, not sandy |
| Exp E2 | 40° C. | Spray-cooking according to the invention 50 msec at 110° C. | Plate heat exchanger 30 sec 92° C. | ++ | Very liquid product, with 150 mPa · s, not sandy |

Rating:
--: bad;
0: moderate;
+: good;
++: very good

It should be understood that various changes and modifications to the presently preferred embodiments described herein will be apparent to those skilled in the art. Such changes and modifications may be made without departing from the spirit and scope of the invention and without diminishing its advantages. It is therefore intended that such changes and modifications are covered by the appended claims.

The invention claimed is:

1. A sterilized or pasteurized liquid enteral nutritional composition having a pH of about 2 to 8 and comprising 10 to 20 g of non-hydrolysed globular protein per 100 ml of the composition, wherein the globular protein is selected from the group consisting of whey protein, pea protein, soy protein, and any mixture thereof.

2. The liquid enteral nutritional composition according to claim 1, further comprising dietary fibre.

3. The liquid enteral nutritional composition according to claim 2, wherein the dietary fiber comprises fructo-oligosaccharides and galacto-oligosaccharides with DP 2-10.

4. The liquid enteral nutritional composition according to claim 1, comprising carrageenans, xanthans, pectins, galactomannans and other high molecular weight (DP>50) indigestible polysaccharides in an amount less than 20% of the weight of the dietary fibre fraction, or less than 1 g/100 ml.

5. The liquid enteral nutritional composition according to claim 1, wherein the composition is an acidic yoghurt or juice with a pH of about 4.

6. The liquid enteral nutritional composition according to claim 1, having a pH≥4 and ≤8.

7. The liquid enteral nutritional composition according to claim 6, wherein the pH is in the range of 4 to 7.

8. The liquid enteral nutritional composition according to claim 1, comprising 11 to 20 g non-hydrolyzed globular proteins per 100 ml of the composition.

9. The liquid enteral nutritional composition according to claim 8, comprising 12-20 g non-hydrolyzed globular proteins per 100 ml of the composition.

10. The liquid enteral nutritional composition according to claim 1, wherein the globular protein comprises whey protein concentrate (WPC), whey protein isolate (WPI), or a mixture thereof.

11. The liquid enteral nutritional composition according to claim 1, obtainable by heat-treatment comprising the consecutive steps of:
  a) adjusting the pH of an aqueous composition comprising non-hydrolysed globular proteins to a value of between about 2 and 8;
  b) converting the composition of non-hydrolysed globular proteins obtained in step a) into an aerosol;
  c) subjecting the aerosol obtained in step b) to a temperature of 100 to 190° C. during a time of about 30 to 300 milliseconds;
  d) flash-cooling the heat-treated aerosol obtained in step c) to a temperature below 85° C. to obtain an aqueous solution comprising heat-treated globular proteins.

12. The liquid enteral nutritional composition according to claim 1, having an energy density of at least 1.5 kcal/ml.

13. The liquid enteral nutritional composition according to claim 1, wherein the non-hydrolysed globular proteins are in an amount at least 85 weight % of the total protein.

14. The liquid enteral nutritional composition according to claim 1, further comprising a non-globular protein selected from the group of casein, caseinate, micellar casein isolate, and mixtures thereof.

15. The liquid enteral nutritional composition according to claim 1, further comprising fat, the fat providing between 20 to 40% of the total energy content of the composition, and/or the composition further comprising carbohydrate, the carbohydrate providing between 30 to 60% of the total energy content of the composition.

16. The liquid enteral nutritional composition according to claim 1, having a viscosity lower than 500 mPa·s, measured at 20° C. at a shear rate of 100 s$^{-1}$.

17. The liquid enteral nutritional composition according to claim 1, the composition being packaged.

18. A method of providing nutrition to a person in need thereof, comprising administering to the person the nutritional composition according to claim 1.

19. The method according to claim 18, wherein the person is an elderly person, a person that is in a disease state, a person that is recovering from a disease state, a person that is malnourished, a sportsman, or an active elderly.

20. A method for the heat-treatment of non-hydrolysed globular proteins, comprising the consecutive steps of:
   a) adjusting the pH of an aqueous composition comprising non-hydrolysed globular proteins to a value of between about 2 and 8;
   b) converting the composition of non-hydrolysed globular proteins obtained in step a) into an aerosol having a particles size that is less than about 30 μm;
   c) subjecting the aerosol obtained in step b) to a temperature of 100 to 190° C. during a time of about 30 to 300 milliseconds;
   d) flash-cooling the heat-treated aerosol obtained in step c) to a temperature below 85° C. to obtain an aqueous solution comprising heat-treated globular proteins,
wherein preferably at least 85 weight % of the non-hydrolysed globular proteins is whey protein.

21. The method according to claim 20, wherein the pH in step a) is adjusted to a value between 4 and 8.

* * * * *